United States Patent [19]
Odello et al.

[11] Patent Number: 5,602,270
[45] Date of Patent: Feb. 11, 1997

[54] PHOSPHAZENE DERIVATIVES AND USE OF SAME AS STABILIZERS FOR OILS AND GREASES BASED ON PERFLUOROPOLYETHERS

[75] Inventors: Paolo Odello, Turin; Walter Navarrini, Boffalora Ticino, both of Italy; Richard D. Chambers, Durham, Great Britain; Costante Corti, Milan, Italy

[73] Assignee: Ausimont S.p.A., Milan, Italy

[21] Appl. No.: 444,428

[22] Filed: May 19, 1995

Related U.S. Application Data

[62] Division of Ser. No. 149,034, Nov. 8, 1993, Pat. No. 5,441,655.

[30] Foreign Application Priority Data

Nov. 10, 1992 [IT] Italy ................... MI92A2569

[51] Int. Cl.$^6$ ................ C07F 9/659; C07F 9/6581; C07F 9/24
[52] U.S. Cl. ................ 558/80; 558/154; 558/157
[58] Field of Search ................ 558/80, 157, 154

[56] References Cited

U.S. PATENT DOCUMENTS

| | | |
|---|---|---|
| 3,214,478 | 10/1965 | Milian . |
| 3,242,218 | 3/1966 | Miller . |
| 3,665,041 | 5/1972 | Sianesi et al. . |
| 3,715,378 | 2/1973 | Sianesi et al. . |
| 3,810,874 | 5/1974 | Mitsch et al. . |
| 3,847,978 | 11/1974 | Sianesi et al. . |
| 4,194,983 | 3/1980 | Paciorek et al. . |
| 4,454,349 | 6/1984 | Tamborski et al. . |
| 4,523,039 | 6/1985 | Lagow et al. . |
| 4,601,843 | 7/1986 | Carr et al. . |
| 4,681,693 | 6/1987 | Gavezotti et al. . |
| 4,814,372 | 3/1989 | Caporiccio et al. . |
| 4,864,047 | 9/1989 | Bezoari . |
| 5,013,405 | 5/1991 | Kar et al. . |
| 5,099,055 | 3/1992 | Kar et al. . |
| 5,219,477 | 6/1993 | Nader et al. . |

FOREIGN PATENT DOCUMENTS

| | | |
|---|---|---|
| 0095725 | 12/1983 | European Pat. Off. . |
| 0145002 | 6/1985 | European Pat. Off. . |
| 0148482 | 7/1985 | European Pat. Off. . |
| 0204144 | 12/1986 | European Pat. Off. . |
| 0287892 | 10/1988 | European Pat. Off. . |
| 0340740 | 11/1989 | European Pat. Off. . |
| 0421747 | 4/1991 | European Pat. Off. . |
| 963579 | 7/1972 | Italy . |
| 1104482 | 2/1968 | United Kingdom . |
| 1226566 | 3/1971 | United Kingdom . |
| WP87/00538 | 1/1987 | WIPO . |

OTHER PUBLICATIONS

European Search Report dated Feb. 21, 1994 for EP 93 11 7770 with Annex.
"Development and Tribological Properties of New Cyclotriphospazene High Temperature Lubricants for Aircraft Gas Turbine Engines," Nader B. S., Kar, K. K., Morgan, T. A., Pawloski, C. E., and Dilling, W. L., *Tribology Transactions*, vol. 35, pp. 37–44 (1992).

*Primary Examiner*—Johann Richter
*Assistant Examiner*—Michael G. Ambrose
*Attorney, Agent, or Firm*—Bryan Cave L.L.P.

[57] ABSTRACT

New phosphazene derivatives, fully substituted by aromatic groups and perfluoropolyethereal chains, are utilized as stabilizers for oils and greases based on perfluoropoyethers. Such derivatives inhibit the degradation process affecting the perfluoropolyethereal chains when these are subjected to high temperatures in an oxidizing atmosphere and in the presence of metals, such as for example aluminium, titanium, vanadium and their alloys, or steels.

10 Claims, No Drawings

PHOSPHAZENE DERIVATIVES AND USE OF SAME AS STABILIZERS FOR OILS AND GREASES BASED ON PERFLUOROPOLYETHERS

This is a division of U.S. application Ser. No. 08/149,034, filed Nov. 8, 1993, now U.S. Pat. No. 5,441,655.

The present invention relates to new phosphazene derivatives and to the use of same as stabilizers for oils and greases based on perfluoropolyethers.

It is known to use fluid perfluoropolyethers as lubricating oils characterized by high performances under extremely severe temperature and load conditions and endowed with an excellent resistance to atmospheric agents and chemical agents in general, as well as to high temperatures. Perfluoropolyether-based greases prepared by addition of a proper thickening agent to the perfluoropolyethereal fluid are known too (see for example Italian patent IT 963,579 or patent application EP 95,825).

A drawback connected with the use of perfluoropolyethers as lubricants is due to the degradation process which the perfluoropolyethereal chains undergo when they are subjected to high temperatures (generally starting from 200°–300°C.) in an oxidizing atmosphere and in the presence of metals, such as e.g. aluminium, titanium, vanadium or their alloys, or steels. Such process causes a decay of the lubricating properties, besides a progressive corrosion of the same metals.

In order to obviate the abovesaid drawback it is known to add little amounts of stabilizing additives to the oils or greases based on perfluoropolyethers. For example, U.S. Pat. No. 4,454,349 describes the use, as stabilizers, of arylphosphines of general formula:

$$\left[ R_fOR_fCF_2 - \bigcirc - \right]_3 P$$

where $R_fRO_f$ is a perfluoropolyethereal group. Such products are obtainable only through an utmostly complex multistep process, which is fully unsuited to an industrial-scale application. In fact, such process comprises, among the various steps, the fluorination of the substrate with $SF_4$ and HF, this being a reaction which raises a lot of problems concerning the plant engineering (low reaction rate, high temperatures and pressures, dangerousness of the reagents, difficult separation of the final products, etc.).

Further arylphosphinic products suitable for being utilized as stabilizers for oils and greases based on perfluoropolyethers are the ones described in U.S. Pat. No. 4,681,693. Such products have a structure analogous with the one of the arylphosphines described in the above-cited U.S. Pat. No. 4,454,349, in which however the perfluoropolyethereal chains are linked to the aromatic ring by means of non-fluorinated groups of various nature. This structural modification permits to simplify the preparation process (in particular, the abovesaid fluorination reaction with $SF_4$ and HF is no longer required), what, however, does not reduce the effectiveness of such products as stabilizers. In spite of this considerable simplification, an industrial-scale production of arylolefins is still complicate and expensive, in consideration of the fact that several intermediate steps are required before the final product can be obtained.

Phosphazenes are products well known in the art. They are characterized by the presence of the $$-N=P-$$

group, which is the basic unit for the formation of both cyclic and linear structures.

For example, U.S. Pat. Nos. 5,015,405 and 5,099,055 described cyclic phosphazene derivatives of formula:

$$(-N=P-)_n \quad (R)_2$$

where n ranges from 3 to 7, while substituents R are fluorinated phenoxy groups or 3-perfluoroalkyl-phenoxy groups, on condition that the ratio of phenoxy groups to 3-perfluoroalkyl-phenoxy groups ranges from 1:5 to 1:1.

Such phosphazene derivatives are per se utilizable as lubricants for high temperatures, or as additives for other lubricants. In particular it is to be pointed out the possibility of utilizing these products as antiwear additives for conventional oils, such as polyglycols, polyphenylethers and polyol esters (see also the article by B. S. Nader, K. K. Kar, T. A. Morgan, C. E. Powloski and W. L. Dilling, published in "Tribology Transactions", 35, 37 (1992)).

The Applicant has now found a new class of phosphazene derivatives, which are endowed with excellent stabilizing properties for oils and greases based on perfluoropolyethers and are preparable according to a relatively economic process, which can be easily practised also on an industrial scale.

Thus, a first object of the present invention are the phosphazene derivatives of cyclic or linear structure, having formula:

$$[(A)_4P]_n-(-N=P-)_m-(A)_n \quad (A)_2 \quad (I)$$

where:
- n is 0 in the case of a cyclic structure, n is 1 in the case of a linear structure;
- m is an integer from 3 to 7;
- groups A, like or different from one another, are selected from:
  (i) R—Q—, in which Q is a divalent group selected from: —O—, —S—, —NR$_1$— (in which R$_1$ is hydrogen or a C$_1$–C$_4$ alkyl), and —NH—NH—; R is a C$_6$–C$_{12}$ aryl group, preferably a phenyl, optionally substituted by one or more, preferably 1 or 2 groups selected from: C$_1$–C$_4$ alkyls, —OR$_2$, —NR$_3$R$_4$, —NO$_2$, —F and —Cl, where R$_2$, R$_3$ and R$_4$ are hydrogen or C$_1$–C$_4$ alkyls;
  (ii) Rf—CH$_2$O(CH$_2$CH$_2$O)$_s$—, wherein: s=0, 1 or 2; R$_f$ is a per-fluoropolyethereal chain having a molecular weight ranging from 400 to 10,000, preferably from 400 to 4,000, and composed of repeating units selected from:
  (a)
  $$(CF-CF_2O) \quad | \quad CF_3$$
  and (CFXO), where X is —F or —CF$_3$;
  (b) (CF$_2$CF$_2$O) nd (CF$_2$O);

(c)

$$(\underset{\underset{CF_3}{|}}{CF}-CF_2O),$$

$(CF_2CF_2O)$ and $(CFXO)$, where X is —F or —$CF_3$;

$$(\underset{\underset{CF_3}{|}}{CF}-CF_2O); \quad (d)$$

(e) $(CYZ-CF_2CF_2O)$, where Y and Z, like or different from each other, are F, Cl or H;

(f) $(CF_2CF_2O)$;

the various repeating units being statistically distributed along the chain;

with the proviso that at least a group of type (i) and at least a group of type (ii) are present in the same molecule; groups R—Q— being also capable of forming, if linked to the same P atom, a cyclic structure of type:

$$\begin{array}{c} R \\ / \phantom{Q} \backslash \\ Q \phantom{RR} Q \\ \backslash \phantom{Q} / \\ -N=P- \end{array}$$

A further object of the present invention are the lubricating compositions comprising:

(a) an oil and a grease based on perfluoropolyethers;

(b) from 0.05 to 3% by weight, preferably from 0.5 to 1% by weight, of a phosphazene derivative of formula (I).

The phosphazene derivatives forming the object of the present invention are in the form of viscous, transparent and colorless fluids, which are fully soluble and easily solubilizable, at the above indicated concentrations, in the perfluoropolyether-based lubricants, and exhibit an excellent thermal stability also at temperatures higher than 300° C.

Among the phosphazene derivatives of formula (I), the preferred ones are those exhibiting a cyclic structure (n=0), having a molar ratio between $R_f$—$CH_2O(CH_2CH_2O)_s$— groups and R—Q— groups ranging from about 0.2 to about 1.8, preferably from about 0.5 to about 1. Within such subclass, the ones in which m is 3 or 4 are particularly preferred.

The perfluoropolyethereal chains $R_f$ can be selected in particular from the following classes:

(a) $\quad T-O-(CFCF_2O)_m(CFXO)_n-CFZ-\quad$ (II)
$\phantom{(a) \quad T-O-(CFCF_2O)_m}|$
$\phantom{(a) \quad T-O-(CFCF_2O)_m}CF_3$ where:

T is a (par)fluoroalkyl group selected from: —$CF_3$, —$C_2F_5$, —$C_3F_7$, —$CF_2Cl$, —$C_2F_4Cl$, —$C_3F_6Cl$; X is —F or —$CF_3$; Z is —F, —Cl or —$CF_3$; m and n are numbers such that the n/m ratio ranges from 0.01 to 0.5 and the molecular weight is in the above-indicated range;

(b) $\quad T'-O-(CF_2CF_2O)_p(CF_2O)_q-CFZ'- \quad$ (III)

where:

$T'$ is a (per)fluoroalkyl group selected from: —$CF_3$, —$C_2F_5$, —$CF_2Cl$, —$C_2F_4Cl$; $Z'$ is —F or —Cl; p and q are numbers such that the q/p ratio ranges from 0.5 to 2 and the molecular weight is in the above indicated range;

(c) $\quad T''-O-(CFCF_2O)_r-(CF_2CF_2O)_s-(CFX''O)_t-CFZ''-\quad$ (IV)
$\phantom{(c)\quad T''-O-(CFCF_2O)_r}|$
$\phantom{(c)\quad T''-O-(CFCF_2O)_r}CF_3$ where:

$T''$ is a (per)fluoroalkyl group selected from: —$CF_3$, —$C_2F_5$, —$C_3F_7$, —$CF_2Cl$, —$C_2F_4Cl$, —$C_3F_6Cl$; $X''$ is —F or —$CF_3$; $Z''$ is —F, —Cl or —$CF_3$; s and t are numbers such that r+s ranges from 1 to 50, the t/(r+s) ratio ranges from 0.01 to 0.05 and the molecular weight is in the above indicated range;

(d) $\quad T'''-O-(CFCF_2O)_u-CF-\quad$ (V)
$\phantom{(d)\quad T'''-O-(CFCF_2O)_u}|\phantom{-CF-}|$
$\phantom{(d)\quad T'''-O-(CFCF_2)}CF_3 \phantom{xx} CF_3$ where:

$T'''$ is —$C_2F_5$ or —$C_3F_7$; u is a number such that the molecular weight is in the above indicated range;

(e) $\quad T^{IV}-O-(CYZ-CF_2CF_2O)_v-CYZ-CF_2-\quad$ (VI)

where:

Y and Z, like or different from each other, are F, Cl or H; $T^{IV}$ is —$CF_3$, —$C_2F_5$ or —$C_3F_7$; v is a number such that the molecular weight is in the above indicated range;

(f) $\quad T^V-O-(CF_2CF_2O)_w-CF_2-\quad$ (VII)

where:

$T^V$ is —$CF_3$ or —$C_2F_5$; w is a number such that the molecular weight is in the above indicated range.

The hydroxy-terminated perfluoropolyethers $R_f$—$CH_2O(CH_2CH_2O)_sH$ are product known in the art. They are preparable by reduction of the —COF end groups contained in the starting perfluoropolyethers, according to what is described for example in U.S. Pat. Nos. 3,847,978, 3,810,874 and 4,814,372. The starting perfluoropolyethers containing —COF end groups are described, for example, in patents GB 1,104,482 (class (a)), U.S. Pat. No. 3,715,378 (class (b)), U.S. Pat. No. 3,242,218 (class (c)), U.S. Pat. No. 3,2.42,218 (class (d)), EP 148,482 (class (el), U.S. Pat. No. 4,523,039 (class (f)), or also in patent application EP 340,740.

The phosphazene derivatives of the present invention are preparable by reacting a perchlorophosphazene of formula $[Cl_4P]_n$—$(N=PCl_2—)_m$—$(Cl)_n$ with the products R—Q—H and $R_f$—$CH_2O(CH_2CH_2O)_sH$ previously treated with a base.

According to a preferred embodiment, the aromatic compound of formula R—Q—H is dissolved in a proper organic solvent, such as diethyl ether or glyme, and is reacted with a base, such as e.g. an alkaline metal iodide (for example NaH or KH), an alkaline metal (for example Na or K), an alkali-metal fluoride (for example KF or CsF), an alkali-metal hydroxide (for example NaOH or KOH), a carbonate or bicarbonate, or an amine (for example a tertiary amine). To the product so obtained, a perchlorophosphazene of formula $[Cl_4P]_n$—$(N=PCl_2—)_m$—$(Cl)_n$ is added in such amounts that the molar ratio of aromatic compound to per chlorophosphazene ranges from 2:1 to 5:1, preferably from 3:1 to 4:1. The reaction temperature generally ranges from the room temperature to the boiling temperature of the utilized solvent, with reaction times which can vary from 1 hour to 10 hours. The resulting product is then reacted with a hydroxy-terminated perfluoropolyether of formula $R_f$—$CH_2O(CH_2CH_2O)_sH$, converted into alcoholate by reaction with one of the bases described above for the aromatic compounds R—Q—H. The molar ratio of perfluoropolyethereal compound to perchlorophosphazene generally ranges from 2:1 to 5:1, preferably from 3:1 to 4:1. The reaction conditions are the same as described above for the reaction with the R—Q—H compounds.

The step sequence is not determinant, wherefore it is also possible to react with perchlorophosphazene first the hydroxy-terminated perfluoropolyether and then the aromatic compound R—Q—H.

As an alternative, the reaction can be conducted in one step by reacting perchlorophosphazene with products R—Q—H and $R_f$—CH$_2$O(CH$_2$CH$_2$O)$_s$H in admixture with each other and previously treated with a base.

The perfluoropolyethers having neutral end groups, utilizable for the formulation of oils and greases are available on the market under the trade-names Fomblin $^{(R)}$ (Ausimont), Krytox $^{(R)}$ (DuPont), Demnum $^{(R)}$ (Daikin), etc. As an example, the following classes of perfluoropolyethers can be cited:

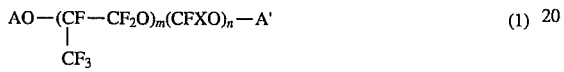
(1)

where X is —F or —CF$_3$; A and A', like or different from each other, are —CF$_3$, —C$_2$F$_5$ or C$_3$F$_7$; m and n are numbers such that the viscosity of the product ranges from 10 to 4000 cSt, the various units being statistically distributed along the chain. These products can be obtained by photooxidation reaction of hexafluoropropene, according to what is described in GB patent 1,104,432, and by successive conversion of the end groups into neutral groups conforming to the process described in GB patent1 226 566.

$$C_3F_7O-(CF-CF_2O)_m-B$$
$$\phantom{C_3F_7O-(}CF_3$$
(2)

where B is —C$_2$F$_5$ or —C$_3$F$_7$, while m is such a number that the viscosity is in the above indicated range. These products can be prepared by ionic oligomerization of the hexafluoropropene epoxide and successive treatment with fluorine according to what is described in U.S. Pat. No. 3,242,21

$$[C_3F_7O-(CF-CF_2O)_m-CFCF_3]_2$$
$$\phantom{[C_3F_7O-(}CF_3$$
(3)

where m is such a number that the viscosity is in the above indicated range. These products are obtained by ionic telomerization of the hexafluoropropene epoxide and by successive photochemical dimerization, according to what is described in U.S. Pat. No. 3,214,478.

(4)

where X is —F or —CF$_3$; A and A', like or different from each other, are —CF$_3$, —C$_2$F$_5$ or —C$_3$F$_7$; m, n and q are numbers such that the viscosity is in the above indicated range. These products are obtainable by photooxidation of mixtures of C$_3$F$_6$ and C$_2$F$_4$ and by subsequent treatment with fluorine according to the process described in U.S. Pat. No. 3,665,041.

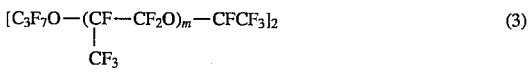
(5)

where A and A', like or different from each other, are —CF$_3$ or —C$_2$F$_5$; p and q are numbers such that the viscosity is in the above indicated range. These products are preparable by photochemical oxidation of C$_2$F$_4$ according to U.S. Pat. No. 3,715,378 and by successive treatment with fluorine according to U.S. Pat. No. 3,665,041.

(6)

where A and A', like or different from each other, are —CF$_3$, —C$_2$F$_5$ or —C$_3$F$_7$; m is such a number that the viscosity of the product is in the above indicated range. These products are obtained according to what is described in patent application EP 148,482.

(7)

where A and A', like or different from each other, are —CF$_3$ or —C$_2$F$_5$; r is such a number that the viscosity of the product is in the above indicated range. These products are obtained according to what is described in U.S. Pat. No. 4,523,039.

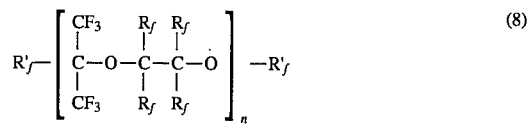
(8)

where R'$_f$ is a perfluoroalkyl, n is a number $\geq 8$, R$_f$ is —F or a perfluoroalkyl. These products are described in patent application WO-87/00538.

A grease based on perfluoropolyethers is typically composed for 15–40% by weight of polytetrafluoroethylene, acting as a thickening agent, and for 60–85% by weight of a liquid perfluoropolyether, besides minor amounts of other products, such as perfluoroalkyl surfactants or polyoxyperfluoro-alkyl surfactants, or other additives known in the art, such as stabilizers, anticorrosive agents, anti-wear agents etc. Additives of this type are usually contained also in oils based on perfluoropolyethers.

The phosphazene derivatives of the present invention, besides exerting a stabilizing action, are also effective as anti-wear additives for oils and greases based on perfluoropolyethers.

The present invention is hereinafter described more in detail in the following examples, which are given merely to illustrate but not to limit the scope of the invention.

EXAMPLE 1

A three-neck flask of 1 liter volume was equipped with a condenser, a dropping funnel, inlet and outlet devices for nitrogen and a magnetic stirrer. All the reaction steps were conducted in an inert nitrogen atmosphere.

A solution of phenol (2.7 g, 28.7 millimoles) in anhydrous diethylether (25 ml) was dropwise added to a suspension of NaH (0.6 g, 25.8 mmoles) in anhydrous diethylether (50 ml). To the resulting mixture, heated at reflux for 1 hour, a solution of hexachlorocyclophosphazene (NPCl$_2$)$_3$ (2.8 g, 8 mmoles) in anhydrous diethyl-ether (30 ml) was added once in a time. The whole was then heated at reflux for 1 hour.

A solution in anhydrous diethylether (30 ml) of hydroxy-terminated Fomblin $^{(R)}$ Y (26.5 g, 29.4 mmoles), having formula R$_f$CH$_2$OH, where R$_f$ is corresponding to formula (II), having an equivalent weight equal to 900 and a ratio of units C$_3$ to units C$_1$ equal to 36.8, was added dropwise to a suspension of NaH (0.6 g, 25.8 mmoles) in anhydrous diethylether (50 ml). The resulting mixture was heated at reflux for 1 hour. Then, the solution obtained from the preceding reaction was added in a unique portion. After a 2-hour heating at reflux, the reaction mixture was treated with 200 ml of demineralized water and then was subjected to extraction with All3 ($CCl_2FCClF_2$). After removal of the solvent by evaporation at reduced pressure, a viscous liquid was obtained, which was purified by distilling-off the unreacted hydroxy-terminated Fomblin (R) Y (at 120° C. and $10^{-3}$ millibar).

The liquid product so purified was distilled at reduced pressure. Two fractions were obtained: the first fraction (6.4 g; b.p. 170°–180° C. at $10^{-3}$ mbar) had an average molar composition corresponding to formula $[(N=P)(—R—Q)(—OCH_2R_f)]_3$ (product 1a); the second fraction (8.7 g; b.p. 180°–200° C. at $10^{-3}$ mbar) had an average molar composition corresponding to formula $[(N=P)(—R—Q)_{0.83}(—OCH_2R_f)_{1.16}]_3$ (product 1b).

The elemental analysis of the products so obtained revealed the absence of chlorine, what confirmed that the substitution reaction had been completed. The average composition was determined by $^1H$ NMR analysis.

EXAMPLE 2

Operating under the same conditions described in example 1, a solution of 3-nitrophenol (3.96 g, 28.5 mmoles) in anhydrous diethylether (25 ml) was added dropwise to a suspension of NaB (0.6 g, 25.8 mmoles) in anhydrous diethylether (50 ml). The resulting mixture was heated at reflux for 1 hour. Then, a solution of $(NPCl_2)_3$ (2.8 g, 8 mmoles) in anhydrous diethylether (30 ml) was added in a unique portion and the whole was heated at reflux for 12 hours.

A solution of the same hydroxy-terminated Fomblin (R) Y utilized in example 1 (26.3 g, 28.9 mmoles) in anhydrous diethylether (30 ml) was added dropwise to a suspension of NaH (0.6 g, 25.8 mmoles) in anhydrous diethylether (50 ml). The resulting mixture was heated at reflux for 1 hour. The solution obtained from the preceding reaction was then added in a unique portion. After a 2-hour heating at reflux, 200 ml of demineralized water were added. Then, an extraction with All3 ($CCl_2FCClF_2$). After removal of the solvents by evaporation at reduced pressure, a viscous liquid was obtained, which was purified by distilling-off the unreacted hydroxy-terminated Fomblin (R) Y (at 120° C. and at $10^{-3}$ mbar) and then by causing the product to pass on a silica gel column, utilizing All3 as an eluent. Obtained were 15 g (conversion: 52%) of a viscous, transparent and colorless liquid, which was identified, through elemental analysis, $^1H$-NMR analysis and $^{31}P$-NMR analysis, as a mixture of substitution products corresponding to the average formula $[(N=P)(—R—Q)(—OCH_2R_f)]_3$ (product 2).

EXAMPLE 3

Operating under the same conditions as described in example 1, a solution of 4-methoxyphenol (3.4 g, 28 mmoles) in anhydrous diethylether (25 ml) was added dropwise to a suspension of NaH (0.6 g, 25.8 mmoles) in anhydrous diethylether (50 ml). The resulting mixture was heated at reflux for 1 hour. Then, a solution of $[NPCl_2]_3$ (3.0 g, 8.6 mmoles) in anhydrous diethylether was added in a unique portion, and the whole was heated at reflux for 12 hours.

A solution of the same hydroxy-terminated Fomblin (R) Y utilized in example 1 (27.0 9, 29.8 mmoles) in anhydrous diethylether (25 ml) was added dropwise to a suspension of NaH (0.6 g, 25.8 mmoles) in anhydrous dtethylether (50 ml). The resulting mixture was heated at reflux for 1 hour. Then, the solution obtained from the preceding reaction was added in a unique portion. After a 2-hour heating at reflux, 200 ml of demineralized water were added. An extraction with All3 ($CCl_2FCClF_2$) was then effected. After removal of the solvents by evaporation at reduced pressure, a viscous liquid was obtained, which was purified by distilling-off the unreacted hydroxy-terminated Fomblin (R) Y (at 120° C. and at $10^{-3}$ mbar) and by causing the product to pass on a silica gel column, using All3 as an eluent. Obtained were 13 g (conversion: 52%) of a viscous, transparent and colorless liquid, which was identified, through elemental analysis, $^1H$-NMR and $^{31}p$-NMR analyses, as a mixture of substitution products corresponding to average formula $[(N=P)(—R—Q)(—OCH_2R_f)]_3$ (product 3).

EXAMPLE 4

A set of tests was conducted in order to check the stability to thermo-oxidation, in the presence of metals, of lubricating compositions containing the phosphazene derivatives prepared in the preceding examples.

Into an apparatus consisting of a glass test-tube equipped with a gas inlet pipe, a vent pipe and a housing for a small disc made of an alloy of Ti, V (4%), Al (6%), there were introduced 50 g of Fomblin (R) Z 25, corresponding to formula $CF_3O—(C_2F_4O)_p(CF_2O)_q—CF_3$ and having a kinematic viscosity equal to 25 cSt at 20° C., additioned with the phosphazene derivative in the amounts indicated in Table I. The test tube was heated to a temperature of 316° C. in an aluminium furnace. The air, after dehumidification and purification, was made to bubble into the perfluoropolyethereal fluid for 72 hours, at a flowrate of 1 liter/hour.

For comparative purposes, also a test on stabilizer-free perfluoropolyether was conducted. The obtained data are reported in Table I. The stabilizer effectiveness was evaluated by measuring, on conclusion of the test, the % variation of weight ($\Delta p^L$) and viscosity ($\Delta \eta^L$) of the lubricant and the L weight variation per unit of surface of the metal alloy sample ($\Delta p^M$).

TABLE I

| Stabilizer | Conc. (% b.wg.) | $\Delta p^L$ (%) | $\Delta \eta^L$ (%) | $\Delta p^M$ (mg/cm$^2$) |
| --- | --- | --- | --- | --- |
| — | — | −100 | n.d. | — |
| Product 1a | 0,80 | −0,9 | +5,7 | 0 |
| Product 1b | 0,90 | −3,3 | −16,1 | 0 |
| Product 2 | 0,85 | −0,7 | +1,8 | +0,13 |
| Product 3 | 0,85 | −15,1 | −0,2 | 0 | n.d.: not determinable.

What is claimed is:

1. Phosphazene derivatives of cyclic or linear structure, having formula:

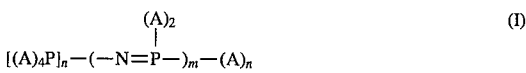

where:

n is 0 in the case of a cyclic structure, n is 1 in the case of a linear structure;

m is an integer from 3 to 7;

groups A, like or different from one another, are selected from:

(i) R—Q—, in which Q is a divalent group selected from: —O—, —S—, —NR$_1$— (in which R$_1$ is hydrogen or a C$_1$–C$_4$ alkyl), and —NH—NH—; R is a C$_6$–C$_{12}$ aryl group, optionally substituted by one or more groups selected from:

$C_1$–$C_4$ alkyls, —$OR_2$, —$NR_3R_4$, —$NO_2$, —F and —Cl, where $R_2$, $R_3$ and $R_4$ are hydrogen or $C_1$–$C_4$ alkyls;

(ii) $R_f$—$CH_2O(CH_2)_s$—, wherein: s=0, 1 or 2; $R_f$ is a perfluoropolyethereal chain having a molecular weight ranging from 400 to 10,000 and composed of repeating units selected from:

(a)

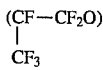

and (CFXO), where X is —F or —$CF_3$;

(b) ($CF_2CF_2O$) and ($CF_2O$);

(c)

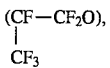

($CF_2CF_2O$) and (CFXO), where X is —F or —$CF_3$;

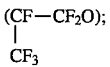 (d)

(e) (CYZ—$CF_2CF_2O$), where Y and Z, like or different from each other, are F, Cl or H;

(f) ($CF_2CF_2O$);

the various repeating units being statistically distributed along the chain;

with the proviso that at least a group of type (i) and at least a group of type (ii) are present in the same molecule; groups R—Q— being also capable of forming, if linked to the same P atom, a cyclic structure of type:

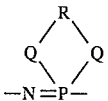

2. The phosphazene derivatives of claim 1, wherein n=0, and wherein the molar ratio of groups $R_f$—$CH_2O(CH_2CH_2O)_s$ to groups R—Q ranges from about 0.2 to about 1.8.

3. The phosphazene derivatives of claim 2, wherein the molar ratio of groups $R_f$—$CH_2O(CH_2CH_2O)_s$— to groups R—Q— ranges from about 0.5 to about 1.

4. The phosphazene derivatives of claim 1, wherein m is 3 or 4.

5. The phosphazene derivatives of claim 1, wherein the perfluoropolyethereal chains $R_f$ have a molecular weight ranging from 400 to 4,000.

6. A phosphazene derivative of cyclic or linear structure having the following formula:

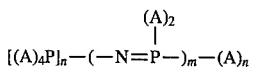

where:

n is 0 in the case of a cyclic structure and n is 1 in the case of a linear structure;

m is an integer from 3 to 7; and the A groups, like or different from each other, are selected from the groups consisting of:

(i) R—Q—, where

Q is a divalent group selected from the group consisting of —O—, —S—, —NH—NH—, and —$NR_1$—, where $R_1$ is hydrogen or a $C_1$–$C_4$ alkyl group; and R is selected from the group consisting of $C_6$–$C_{12}$ aryl groups, and $C_6$–$C_{12}$ aryl groups substituted by one or more groups selected from the group consisting of $C_1$–$C_4$ alkyls, —$OR_2$, —$NR_3R_4$, —$NO_2$, —F, and —Cl, where $R_2$, $R_3$, and $R_4$ are selected from the group consisting of hydrogen or $C_1$–$C_4$ alkyls; and (ii) $R_f$—$CH_2O(CH_2CH_2O)_s$—; where:

s is equal to 0, 1, or 2; and $R_f$ is a polyethereal chain having a molecular weight ranging from 400 to 10,000 and composed of repeating units selected from the group consisting of:

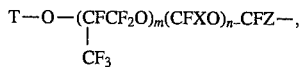 (a)

where:

T is a fluoroalkyl group selected from the group consisting of —$CF_3$, —$C_2F_5$, —$C_3F_5$, —$C_3F_7$, —$CF_2Cl$, —$C_2F_4Cl$, and —$C_3F_6Cl$;

X is —F or —$CF_3$;

Z is —F, —Cl or —$CF_3$; and m and n are numbers such that the n/m ratio ranges from 0.01 to 0.5, and the molecular weight ranges from 400 to 10,000;

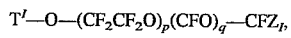 (b)

where:

$T'$ is a fluoroalkyl group selected from the group consisting of —$CF_3$, —$C_2F_5$, —$CF_2Cl$, and —$C_2F_4Cl$;

$Z'$ is —F or —Cl; and p and q are numbers such that the q/p ratio ranges from 0.5 to 2 and, the molecular weight ranges from 400 to 10,000;

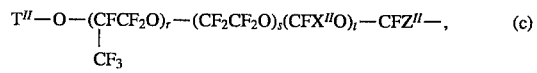 (c)

where:

$T''$ is a fluoroalkyl group selected from the group consisting of —$CF_3$, —$C_2F_5$, —$C_3F_7$, —$CF_2Cl$, —$C_2F_4Cl$, and —$C_3F_6Cl$;

$X''$ is —F or —$CF_3$;

$Z''$ is —F, —Cl, or —$CF_3$; and r, s and t are numbers such that (r+s) ranges from 1 to 50, the t/(r+s) ratio ranges from 0.1 to 0.05, and the molecular weight is from 400 to 10,000;

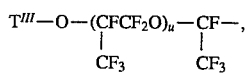 (d)

where:

$T'''$ is —$C_2F_5$, or —$C_3F_7$; and u is a number such that the molecular weight ranges from 400 to 10,000;

 (e)

where:

Y and Z, equal or different, are F, Cl or H;

$T^{IV}$ is selected from the group consisting of —$CF_3$, —$C_2F_5$, and —$C_3F_7$; and v is a number such that the molecular weight ranges from 400 to 10,000; and $$T^V\text{—}O\text{—}(CF_2CF_2O)_w\text{—}CF_2\text{—}, \quad (f)$$

where:

$T^V$ is —$CF_3$, or —$C_2F_5$; and w is a number such that the molecular weight ranges from 400 to 10,000;

such that at least one group of type (i) and at least one group of type (ii) are present in the phosphazene derivative molecule; and such that groups —R—Q, if linked to the same phosphorus atom, are capable of forming a cyclic structure with the following formula:

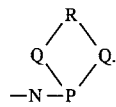

7. The phosphazene derivatives of claim 6, wherein the molar ratio of groups $R_f$—$CH_2O(CH_2CH_2O)$, to groups R—Q ranges from about 0.2 to about 1.8.

8. The phosphazene derivatives of claim 7, wherein the molar ratio of groups $R_f$—$CH_2O(CH_2CH_2O)$, to groups R—Q ranges from about 0.5 to about 1.

9. The phosphazene derivatives of claim 6, wherein m=3 or 4.

10. The phosphazene derivatives of claim 6, wherein the perfluoropolyethereal chain $R_f$ has a molecular weight ranging from 400 to 4,000.

* * * * *

UNITED STATES PATENT AND TRADEMARK OFFICE
CERTIFICATE OF CORRECTION

PATENT NO. : 5,602,270
DATED : February 11, 1997
INVENTOR(S) : Paolo Odello et al.

It is certified that error appears in the above-identified patent and that said Letters Patent is hereby corrected as shown below:

Column 9, Line 4: Delete: "$R_f\text{-}CH_2O(CH_2O)_s\text{-}$," Insert: -- $R_f\text{-}CH_2O(CH_2CH_2O)_s\text{-}$, --

Column 9, Line 41: Delete: "$R_f\text{-}CH_2O(CH_2CH_2O)$,"

Insert: -- $R_f\text{-}CH_2O(CH_2CH_2O)_s$ --

Column 10, Line 19: Delete: "$\text{-}C_3F_5$,"

Column 10, Line 28: Delete: "$T^I\text{-}O\text{-}(CF_2CF_2O)_p(CFO)_q\text{-}CFZ_I$,"

Insert: -- $T^I\text{-}O\text{-}(CF_2CF_2O)_p(CFO)_q\text{-}CFZ^I\text{-}$, --

Column 12, Line 2: Delete "$R_f\text{-}CH_2O(CH_2CH_2O)$,"     Insert: -- $R_f\text{-}CH_2O(CH_2CH_2O)_s$ --

Column 12, Line 5: Delete "$R_f\text{-}CH_2O(CH_2CH_2O)$,"     Insert: -- $R_f\text{-}CH_2O(CH_2CH_2O)_s$ --

Signed and Sealed this

Twenty-seventh Day of January, 1998

*Attest:*

BRUCE LEHMAN

*Attesting Officer*     *Commissioner of Patents and Trademarks*